United States Patent
Carpenter et al.

[11] Patent Number: 5,876,419
[45] Date of Patent: Mar. 2, 1999

[54] STENT AND METHOD FOR MAKING A STENT

[75] Inventors: Kenneth W. Carpenter, Del Mar; Leo R. Roucher, Jr., Escondido; Eugene J. Jung, Jr., San Diego; Erich H. Wolf, Vista; Thomas A. Steinke, San Diego; Robert J. Duffy, Poway; Philip L. Baddour, San Diego, all of Calif.

[73] Assignee: Navius Corporation, San Diego, Calif.

[21] Appl. No.: 950,969

[22] Filed: Oct. 15, 1997

Related U.S. Application Data

[63] Continuation-in-part of Ser. No. 720,714, Oct. 2, 1976, which is a continuation-in-part of Ser. No. 557,725, Nov. 13, 1995, Pat. No. 5,643,314.

[51] Int. Cl.⁶ .................................................. A62M 29/00
[52] U.S. Cl. ................................ 606/198; 623/1; 623/12
[58] Field of Search .............................. 606/1, 108, 192, 606/194, 195, 198, 200; 623/1, 12

[56] References Cited

U.S. PATENT DOCUMENTS

| | | |
|---|---|---|
| 3,278,176 | 10/1966 | Abolins . |
| 3,842,441 | 10/1974 | Kaiser . |
| 4,214,587 | 7/1980 | Sakura, Jr. . |
| 4,434,797 | 3/1984 | Silander . |
| 4,512,338 | 4/1985 | Balko et al. . |
| 4,553,545 | 11/1985 | Maass et al. . |
| 4,732,152 | 3/1988 | Wallsten et al. . |
| 4,733,665 | 3/1988 | Palmaz . |
| 4,739,762 | 4/1988 | Palmaz . |
| 4,740,207 | 4/1988 | Kreamer . |
| 4,776,337 | 10/1988 | Palmaz . |
| 4,793,348 | 12/1988 | Palmaz . |
| 4,800,882 | 1/1989 | Gianturco . |
| 4,856,516 | 8/1989 | Hillstead . |
| 4,878,906 | 11/1989 | Lindemann et al. . |
| 4,886,062 | 12/1989 | Wiktor . |
| 4,907,336 | 3/1990 | Gianturco . |
| 4,913,141 | 4/1990 | Hillstead . |
| 4,969,458 | 11/1990 | Wiktor . |
| 5,019,090 | 5/1991 | Pinchuk . |
| 5,344,426 | 9/1994 | Lau et al. . |
| 5,383,892 | 1/1995 | Cardon et al. . |
| 5,403,341 | 4/1995 | Solar . |
| 5,441,515 | 8/1995 | Khosravi et al. . |
| 5,449,373 | 9/1995 | Pinchasik et al. . |
| 5,549,662 | 8/1996 | Fordenbacher ........................... 606/198 |
| 5,618,299 | 4/1997 | Khosravi et al. ........................ 606/198 |
| 5,643,314 | 7/1997 | Carpenter et al. ....................... 606/198 |

FOREIGN PATENT DOCUMENTS 0 382 014  8/1990  European Pat. Off. .

Primary Examiner—William Lewis
Attorney, Agent, or Firm—Nydegger & Associates

[57] ABSTRACT

The present invention is a stent for insertion into an artery or other vessel. The stent is formed from a series of tubular shaped bands each formed with a first end which overlaps a second end. The overlap between the first and second ends is variable and allows each band to move between a contracted configuration and a fully expanded configuration which are within the elastic limits of the band. Each band includes a plurality of receivers and a first tab on a first edge of the band to secure each band at or near the fully expanded configuration and allow the stent to conform to the contours of the vessel. The bands are distributed along a substantially common axis to form a tube interconnected by a pair of elongated strips. In use, the stent is placed over a balloon catheter and compressed to adopt the contracted configuration. The stent may be maintained in the contracted configuration by a retainer. The balloon catheter and stent are then advanced through a placement catheter to a target site where the balloon is partially inflated to free the stent for expansion to an equilibrium configuration. The balloon may then be more fully inflated to further expand any of the bands in the stent to suit the needs of the patient. The balloon is then deflated and removed, leaving the expanded stent to support that target site.

28 Claims, 4 Drawing Sheets

STENT AND METHOD FOR MAKING A STENT

This application is a continuation-in part of applicants' copending application Ser. No. 08/720,714, filed on Oct. 2, 1996, entitled "Improved Stent", which is a continuation-in part of applicants' application Ser. No. 08/557,725, filed Nov. 13, 1995, entitled "Self-Expanding Stent," which issued as U.S. Pat. No. 5,643,314.

FIELD OF THE INVENTION

The present invention pertains generally to devices which are used for treatment of weakened or clogged arteries and other internal vessels. More specifically, the present invention pertains to devices which can be expanded within an artery or other vessel to prevent occlusion of the vessel. The present invention is particularly, but not exclusively, useful as a flexible, secure stent for insertion into an artery or vessel to support the vessel wall.

BACKGROUND OF THE INVENTION

The use of stents within vessels, such as arterial vessels, is well known. Generally, devices of this type are inserted into a vessel to support the vessel wall, and thus prevent the wall from collapsing and occluding the vessel. Alternatively, in a procedure commonly referred to as vascular repaving, stents may be inserted into a weakened portion of a vessel to prevent internal pressure within the vessel from causing the vessel wall to rupture. Accordingly, stents may be useful whenever a vessel wall has become weakened (such as by disease) or when the vessel becomes clogged (such as by the buildup of plaque), or whenever surrounding tissue (such as a tumor) is applying pressure to the outside of a vessel which may cause the vessel to collapse.

The benefits associated with the use of stents has resulted, not surprisingly, in the increased use of stents to treat an ever increasing number of maladies. As a result, a wide variety of differing stent designs have been developed, each of which may be more, or less, appropriate for the treatment of a particular condition. A contributing factor to the proliferation of differing stent types has been the problematic conditions faced as part of the design and fabrication of a beneficial stent. For example, it is readily appreciated that the operational environment into which a stent is to be placed may vary widely from the idealized conditions of a laboratory. Specifically, the vessel into which the stent is to be placed may be curved or otherwise tortuous. In such cases, insertion of an inflexible stent may be undesirable or even impossible. This particular difficulty is often avoided by the use of a shorter stent, or even a series of shorter stents. In either case, however, the treatment may be complicated or the efficacy of the treatment may be reduced.

Tapered vessels present another aspect of stent design which can be of concern. Tapered vessels, are of course, not uncommon and may even occur in combination with the curved vessel discussed in the preceding section. In cases with tapered vessels, the use of a stent which cannot conform to the changing diameter of the vessel may be problematic. Once again, the use of a series of shorter stents is possible, but this necessarily complicates the course of treatment.

The particular treatment site may also subject the stent to a relatively large compressive load. In such cases the use of a stent which recoils under the load would be inappropriate. The solution for many cases of this type is the utilization of a stronger, or more robust, stent. The use of a stronger stent may not be possible, however, if the stent is required to provide a high degree of flexibility such as when placement within a curved or tapered vessel is required.

Practice has also shown that the use and placement of stents in small vessels is particularly difficult. More specifically, at present, most stents are designed to be delivered in an un-expanded state and then expanded, in-situ, to support the vessel at the target site. In small vessels (generally those with a diameter of less than three millimeters), there may not be adequate room to allow passage of the stent. This may be so even with the stent in its unexpanded state. The use of smaller stents is possible, but may in itself be difficult if the stent is not strong enough to support the intended compressive load.

In light of the above, it is an object of the present invention to provide a vascular stent which can be inserted into a vessel to support the vessel wall. Another object of the present invention is to provide a vascular stent which can withstand a relatively large compressive load without recoiling. Another object of the present invention is to provide a vascular stent which can be inserted into relatively small vessels. Still another object of the present invention is to provide a vascular stent which expands substantially iso-concentrically to more nearly replicate the original lumen of a vessel and can be utilized in a curved or tapered vascular segment. Yet another object of the present invention is to provide a stent which reliably stays in position in the vessel. Still another object of the present invention is to provide a vascular stent which is relatively easy to manufacture, simple to operate and comparatively cost effective.

SUMMARY

The present invention provides a stent for placement into an artery or other vessel within a patient. Structurally, the present invention includes a series of interconnected tubular shaped bands. As detailed below, the interconnected bands expand to closely replicate the original lumen of the vessel, bend to fit a curved or tapered vascular segment and reliably stay in position in the vessel.

Each band is formed to have a first edge, a second edge, an inner surface and an outer surface. Each band is also non-continuous and includes a first end which overlaps at least a portion of a second end so that a portion of the inner surface of each band overlays and contiguously contacts a portion of the outer surface of the same band. For each band, the first end is movable relative to the second end to reconfigure the band between a tubular shaped, contracted configuration and a tubular shaped, fully expanded position.

Basically, the first end of each band moves along a path over the outer surface of the band, which is substantially concentric with a path of the second end of the band as it moves along the inner surface of the band. The movements of the first end and second end of the band along their respective paths create an overlap region which is able to increase or decrease. Functionally, this allows each band to move substantially iso-concentrically between the contracted configuration having a first diameter and the fully expanded configuration having a second diameter.

As provided herein, each band can be made of a resilient material and can be formed so that, absent some restraint, each band expands from the contracted position and approaches the fully expanded position. The amount that each band expands, absent restraint, can be controlled during the manufacture of the stent to suit the particular use of the stent.

For example, the plurality of interconnected bands can be manufactured from a thin sheet of resilient material such as stainless steel. The pattern of the bands in the stent can be chemically milled into the thin sheet. Next, the stent is rolled on a mandrel into a tubular shape with the first end of each band overlapping its second end. Preferably, the stent is rolled so that movement of each band between the contracted configuration and the fully expanded configuration is within the elastic limits of each band and an equilibrium configuration for each band is between the contracted configuration and the fully expanded configuration.

The term "equilibrium configuration" as used herein means the configuration each band is manufactured to assume in the absence of an external force to the band.

The term "elastic limit" as used herein means the point beyond which plastic deformation is present after the release of a load to the band. For example, if the band is contracted past its elastic limit, the band will not expand to the equilibrium configuration without providing an external force. Similarly, if the band is expanded past its elastic limit, the band will not contract to the equilibrium configuration without providing an external force. As long as the band is deflected within its elastic limits, the band will return to its equilibrium configuration in the absence of an external force.

At least one of the bands and more preferably all of the bands include a first tab and at least one receiver disposed proximate the first edge to retain the stent in the vessel. Structurally, the first tab is positioned proximate one of the ends, while the receiver is positioned proximate the other end. The first tab includes an engagement section that is on a plane which is substantially perpendicular to a central axis of the band. Stated another way, the engagement section extends substantially radially from proximate the first edge. This allows the engagement section to securely engage the receiver and inhibit the tubular band from retracting toward the contracted configuration.

Preferably, the first tab is positioned proximate to the second end so that the engagement section is directed radially outward and does not interfere with the operation of a balloon used to install the stent. Further, the first tab can be folded above a portion of the outer surface to hold the first end of the band against the inner surface.

At least one band can include a plurality of receivers positioned at predetermined positions so that each band may be retained at a plurality of intermediate expanded configurations between the contracted and fully expanded configurations. In one embodiment of the present invention, each of the retainers is a notch in the first edge having a notch depth and shaped to receive the engagement section of the first tab. Importantly, each notch is shaped to allow the tab to move past the notch as the band expands but inhibit the tab from moving past the notch when the band is subject to compression.

In the embodiment with a plurality of receivers, the engagement section of the tab sequentially engages the receivers as the band expands and inhibits the band from returning towards the contracted configuration when the band is subject to compression. Typically, the receivers are positioned to engage the first tab at a variety of positions less than the fully expanded configuration.

Optimally, each band includes a second tab and a protruding section. The second tab projects from the second edge, proximate second end and substantially opposite the first tab. The second tab can be folded radially outward and over a portion of the outer surface of the band to hold the second end to the outer surface. The protruding section extends outwardly from the second edge proximate the first end a section distance which is approximately equal to the notch depth. The protruding section is located opposite the receivers and cooperates with the second tab to draw the first tab into engagement with the receivers.

Importantly, the first and second tabs allow the first and second ends of the band to move along their respective, substantially concentric paths. In this fashion, the ability of the band to move between the contracted configuration and the fully expanded configuration, by changing the overlap region between the first end and second end, is preserved.

Operationally, the stent while at its contracted configuration is first positioned to surround a portion of an inflatable balloon catheter. At this diameter, a retainer, e.g. an adhesive, may be used to selectively secure the first end of each band to its respective outer surface to hold the bands in the contracted configuration. This may also lock the stent over the balloon catheter. A guide catheter is then inserted into the patient's body. The guide catheter is formed with a lumen and the stent and balloon are inserted into the lumen and advanced into the patient's body.

Inside of the patient's body, the stent and balloon catheter are advanced distally out of the placement catheter. The stent and balloon catheter are then advanced until the target site has been reached. With the stent positioned at the target site, the balloon is first partially inflated. This initial partial inflation of the balloon applies an expansive force to the inner surface of each of the bands that overcomes the retainer retaining the bands and expands the stent to the equilibrium configuration.

When freed, the bands, if made of a resilient material, undergo an initial expansion from the contracted configuration to its equilibrium configuration. Once the initial expansion is complete, the balloon can be further inflated to further expand each of the bands, if necessary. In particular, each of the bands is expanded until the first tab of each band has engaged with one of the receivers that are formed in that particular band. Depending on which receiver is engaged, the stent will assume one of the intermediate expanded configurations or the fully expanded configuration. Further, the stent is securely maintained in position since the engagement section of each band securely engages one of the receivers as a result of the unique cooperation and design of the first tab, the second tab, the receivers and the protruding section.

Subsequently, the balloon may be deflated and removed or re-inflated to further expand specific, partially expanded bands within the stent. As can be easily appreciated, the differential expansion of the bands allows the stent to adapt to tapered or otherwise irregular vessels. In all cases, with the expanded stent positioned to support the vessel wall at the target site, the balloon is deflated and the balloon and placement catheter are withdrawn from the vessel to complete the procedure.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION

Figure 1:
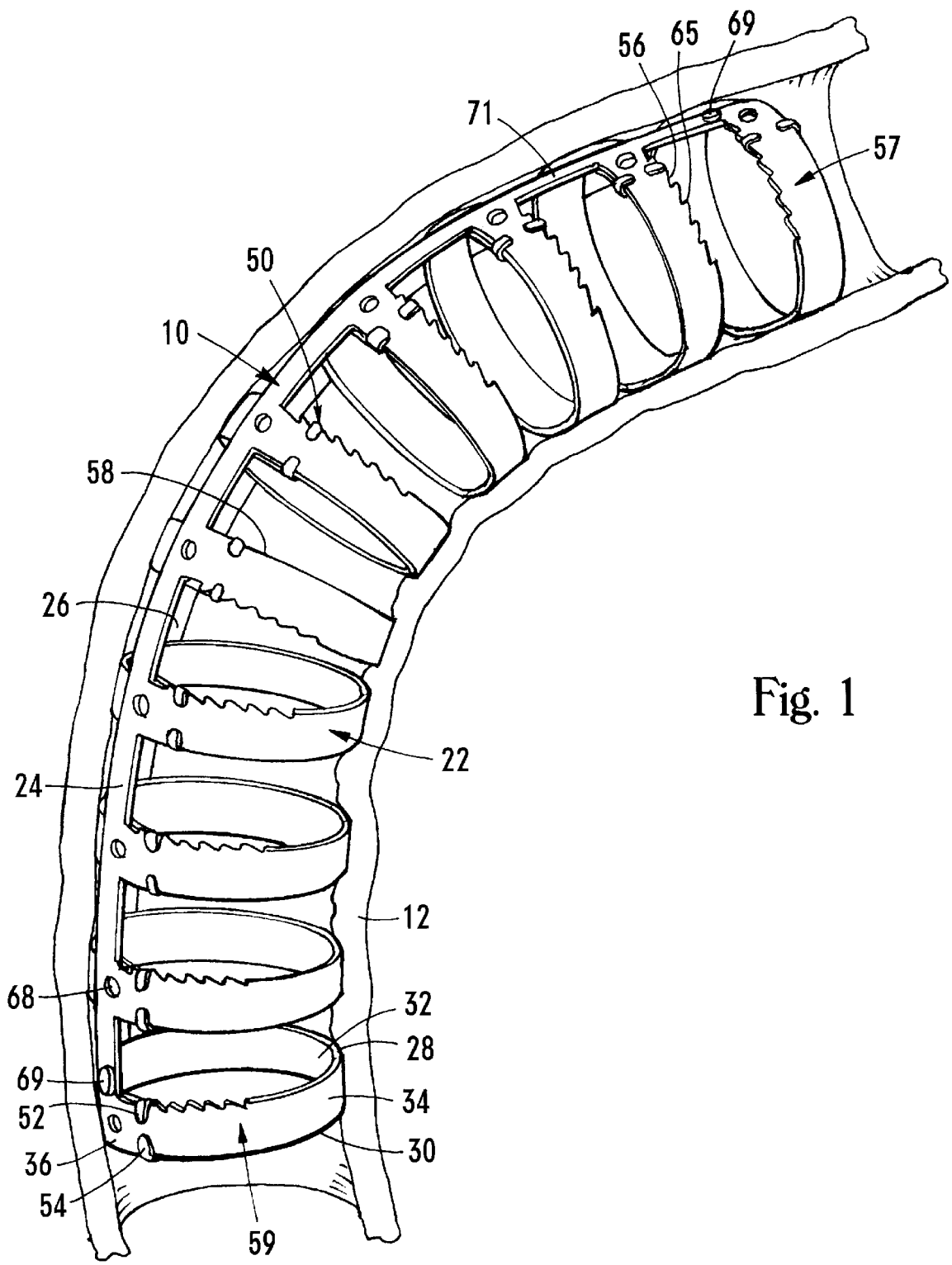
FIG. 1 is a representation of a stent having features of the present invention, positioned within a vessel of a patient.

Referring initially to FIG. 1, a stent 10 for structurally supporting the wall of a vessel 12 in accordance with the present invention is disclosed herein. For purposes of illustration, the stent 10 is shown operationally positioned in a vessel 12 in a patient. It should be appreciated, that the stent 10 is useful in vessels 12 throughout the vascular system of the patient and may be introduced into the vessel 12 wherever it is most convenient to do so.

Figure 2:
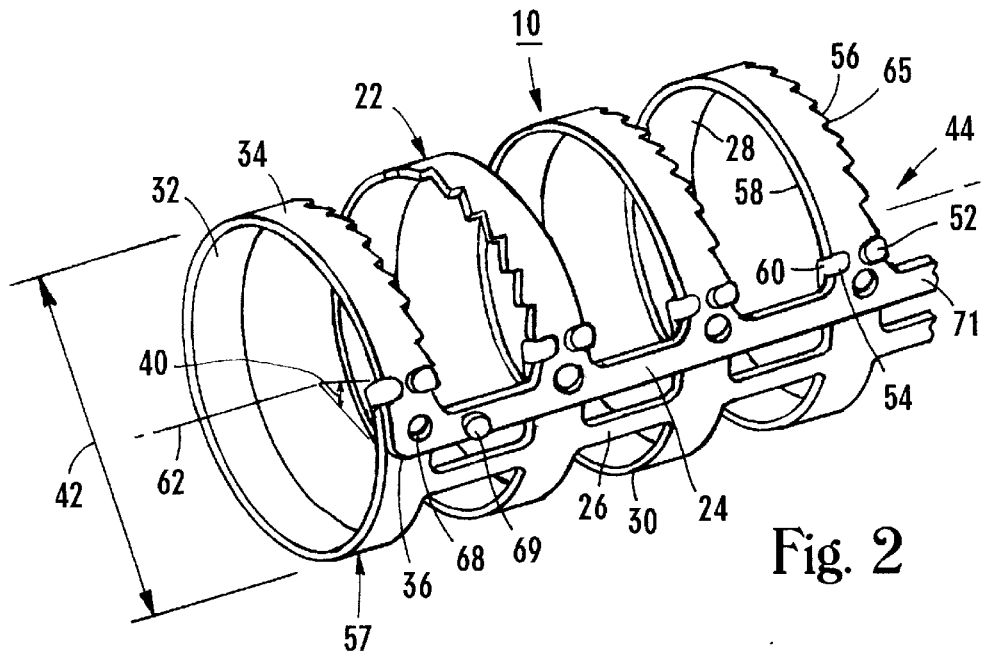
FIG. 2 is an isometric view of the stent FIG. 1 shown in a fully expanded configuration.
Figure 3:
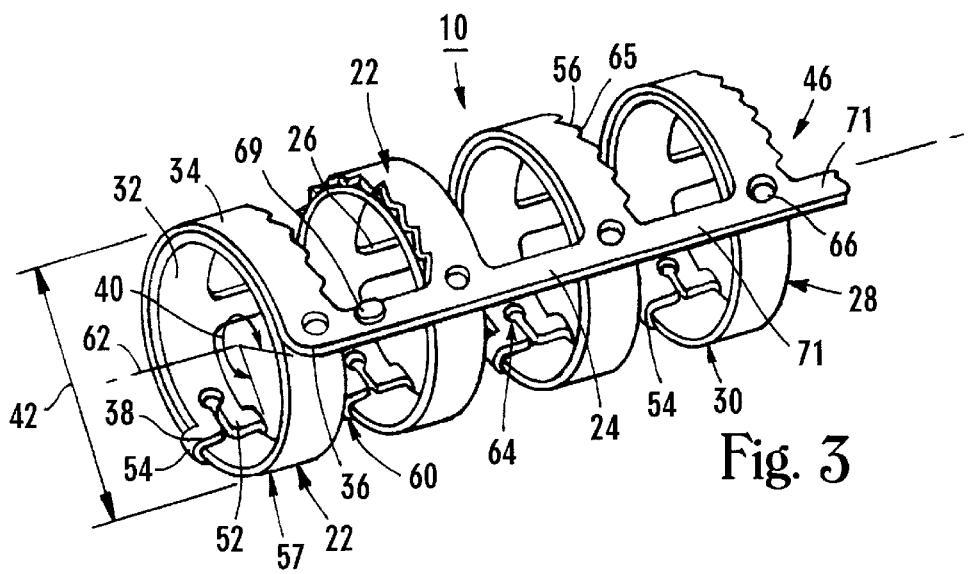
FIG. 3 is an isometric view of the stent of FIG. 1 in an equilibrium configuration.
Figure 4:
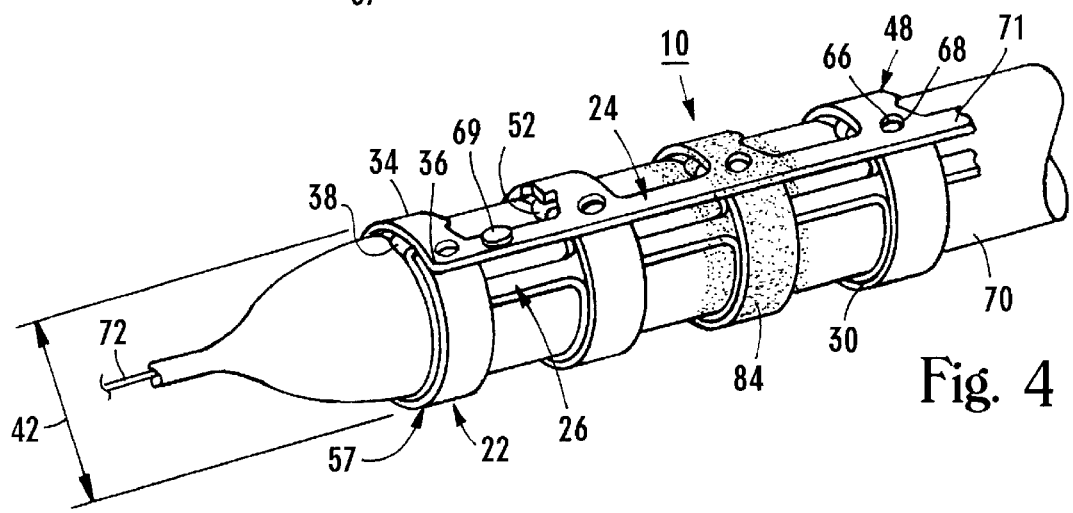
FIG. 4 is an isometric view of the stent of FIG. 1 shown in a contracted position on a balloon that is deflated.
Figure 5:
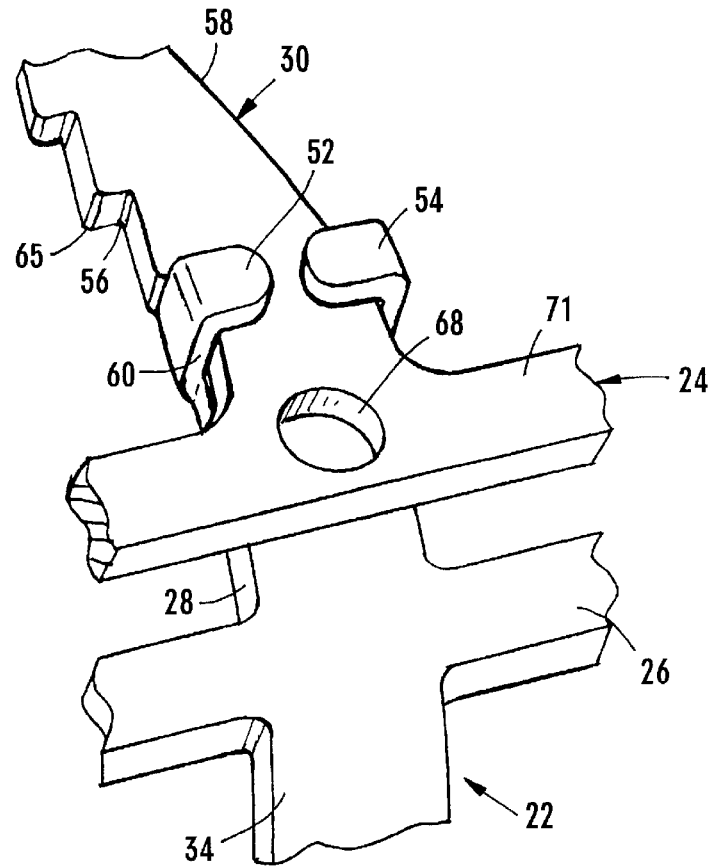
FIG. 5 is an expanded, isometric view of a portion of the stent of FIG. 2.

Referring now to FIGS. 2–4, it may be seen that the stent 10 is an elongated tube formed from a series of tubular shaped bands 22. The bands 22 are interconnected by a first elongated strip 24 and a second elongated strip 26. Each band 22 is formed to have a substantially circular shape, a first edge 28, a second edge 30, an inner surface 32 and an outer surface 34. Each band 22 is formed to be non-continuous. As a result, each band 22 has a first end 36 and a second end 38.

The first end 36 and second end 38 partially overlap each other so that a portion of the inner surface 32 of each band 22 overlays and contiguously contacts a portion of the outer surface 34 of the same band 22. Importantly, for each band 22, the first end 36 is moveable over the outer surface 34 and the second end 38 is moveable over the inner surface 32.

The movement of the first end 36 and second end 38 provides an overlap region 40 between the first end 36 and the second end 38 of each band 22. Increasing or decreasing the overlap region 40 of the band 22 causes a corresponding increase or decrease in the diameter 42 of the band 22.

For each band 22, the relationship between the overlap region 40 and the diameter 42 may be more easily appreciated by comparison between FIG. 2, where the bands 22 are shown in a fully expanded configuration 44, FIG. 3, where the bands 22 are shown in an equilibrium configuration 46, and FIG. 4, where the bands 22 are shown in a contracted configuration 48. Specifically, it may be seen that the overlap region 40 of FIG. 2 increases in FIG. 3 and further increases in FIG. 4. It may also be seen that the diameter 42 in FIG. 2, decreases in FIG. 3 and further decreases in FIG. 4. Thus, movement of the first end 36 relative to the second end 38 varies the overlap region 40 and allows the bands 22 to move between the fully expanded configuration 44 shown in FIG. 2 and the contracted configuration 48 shown in FIG. 4.

Returning to FIGS. 2–4, at least one of the bands 22 can include a first tab 52, a second tab 54, a plurality of receivers 56 and a protruding section 58 to secure the band 22 at the fully expanded configuration 44 or one of the intermediate expanded configurations 50 between the contracted configuration 48 and the fully expanded configuration 44. For the purposes of the present invention, any number of the bands 22 can include these components. Preferably, referring to FIG. 1, each band 22 includes these components so that the stent 10 is securely retained in the vessel 12 and each band 22 of the stent 10 can be expanded to conform to the contours of the vessel 12.

In the embodiment shown in the Figures, the first tab 52 and second tab 54 are positioned proximate the second end 38. The first tab 52 projects from the first edge 28 while the second tab 54 projects from the second edge 30. The first tab 52 includes a engagement section 60 for interacting with the receivers 56 and retaining the band 22 expanded from the contracted position 48 in one of the intermediate expanded configurations or the fully expanded configuration 44. The engagement section 60 is disposed in a plane which is substantially perpendicular to a central axis 62 of the bands prior to installation into the vessel 12. Stated another way, the engagement section 60 extends substantially radially from proximate the first edge 28. This design of the engagement section 60 ensures good contact between the engagement section 60 and each receiver 56. Additionally, because of this design, the engagement section 60 is free to pivot or move relative to the first edge 28 past the receivers 56.

In the embodiment shown in the Figures, both the first tab 52 and the second tab 54 are folded radially outward and over a portion of the outer surface 34 and the engagement section 60 of the first tab 52 is defined by the radial outward portion of the first tab 52.

Functionally, first tab 52 and second tab 54 function as a clasp which hold the first end 36 against the outer surface 34. Importantly, the first tab 52 and the second tab 54 flex and bend to allow each band 22 to move between the contracted configuration 48 of FIG. 4 and the fully expanded configuration 44 of FIG. 2.

Preferably, at least a portion of the first tab 52 and the second tab 54 are annealed to allow the tabs 52, 54 to be folded radially outward and over the outer surface 34. Further, the annealing of the tabs 52, 54 may provide additional flexibility as the first tab 52 moves over the receivers 56 and as the stent 10 flexes in the vessel 12.

Figure 6:
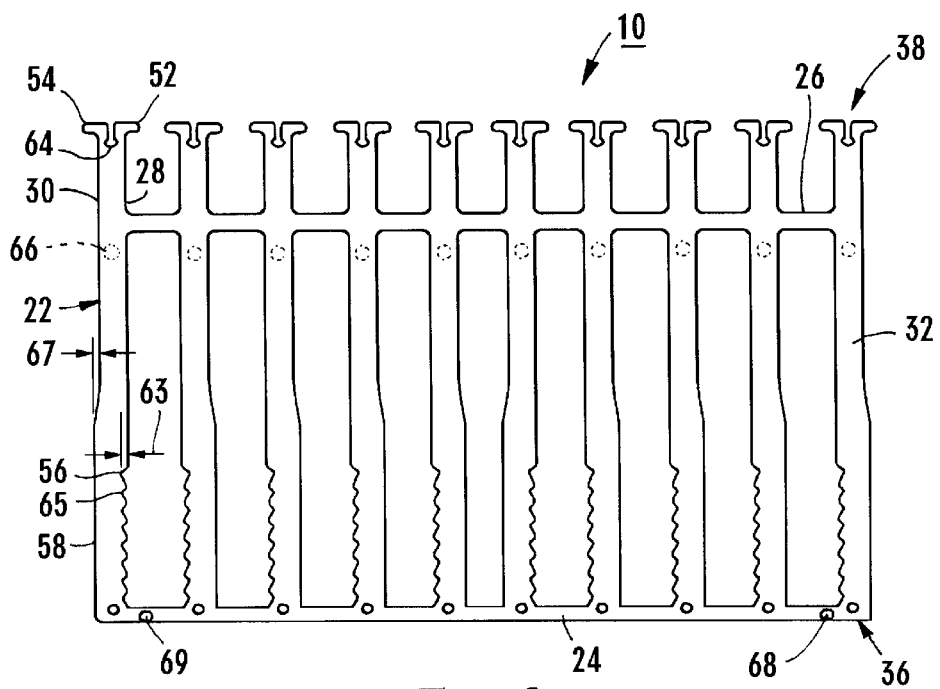
FIG. 6 is a front plan view of a first embodiment of a thin sheet prior to being shaped into a stent having features of the present invention.
Figure 7:
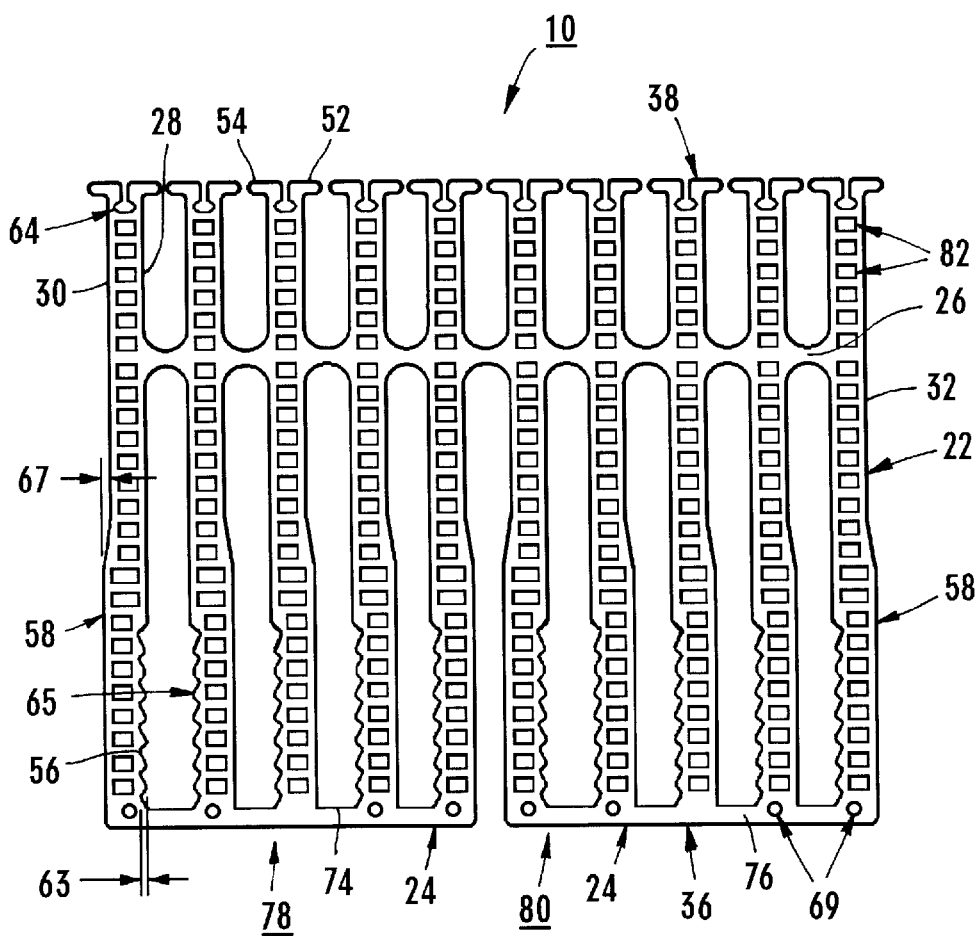
FIG. 7 is a front plan view of a second embodiment of a thin sheet prior to being shaped into a stent having features of the present invention.

As can best be seen in FIGS. 6 and 7, a relief 64, e.g., a slot, can be disposed between the first tab 52 and the second tab 54 to provide additional flexibility to the tabs 52, 54 during expansion of the bands 22 and during use in the vessel 12. Basically, the relief 64 allows the tabs 52, 54 to separate as the first tab 52 moves over each receiver 56 and causes the tabs 52, 54 to pull together therebetween.

The structural details of the band 22 may be more fully appreciated by reference to FIGS. 6 and 7 where a plurality of bands 22 are shown in an unrolled configuration and the first tab 52 and the second tab 54 have not been folded radially outward and over the outer surface 34. Further, the receivers 56 and protruding lip 58 are also clearly visible from FIGS. 6 and 7.

The receivers 56 receive and retain the first tab 52. The receivers 56 can be implemented in a number of ways. For example, in the embodiment shown in the Figures, each receiver 56 is a notch formed into the first edge 28 of the band 22 having a notch depth 63. In the embodiment shown in the Figures, the notches are shaped to receive the engagement section 60 of the first tab 52 and have a notch depth 63 of between about 0.002 inches to 0.010 inches. Referring to FIG. 6, each receiver 56 is a notch which is shaped somewhat similar to an inclined ramp to facilitate movement of the first tab 52 in one direction over the notch and inhibit movement in the other direction. Preferably, a leading edge 65 of each notch is rounded to minimize trauma to the vessel 12.

Referring to FIG. 1, the notches are positioned at predetermined positions on the first edge 28. As a result, as the first end 36 of the band 22 moves over the outer surface 34 to expand the band 22, the first tab 52 sequentially engages each of the notches. The engagement between the first tab 52 and each of the notches allows each band 22 to expand by sequentially engaging each successive notches but inhibits subsequent contraction towards the contracted configuration 48 (shown in FIG. 4).

Referring to FIG. 2, when the first tab 52 engages the notch closest to the first end 36, the band 22 in the fully expanded configuration 44. Similarly, referring to FIG. 1 when the first tab 52 engages one of the remaining notches, the band 22 is in one of intermediate expanded configurations 50. Preferably, the notches are positioned proximate the first end 36 so that contraction towards the contracted configuration 48 (shown in FIG. 4) is only inhibited when each band 22 nears the fully expanded configuration 44 of FIG. 2.

As shown in FIG. 1, the notches on a distal band 57 and a proximal band 59 of the stent 10 are directed towards each other to minimize trauma to the patient during insertion into the vessel 12.

Referring to FIGS. 6 and 7, the protruding section 58 extends a section distance 67 from the second edge 30 of each band 22 proximate the first end 36. The protruding section 58 extends opposite the receivers 56 and cooperates with the second tab 54 to draw the first tab 52 into each receiver 56 so that the first tab 52 is securely retained in each receiver 56. Preferably, the section distance 67 is substantially equal to the notch depth 63 so that the second tab 54 will pull the first tab 52 into the notches. In the embodiment shown in the Figures, the notches have a notch depth 63 which is substantially equal to about 0.002 to 0.010 inches. Thus, for the embodiments shown in the Figures, the protruding lip 58 can extend from the second edge 30 a lip distance 67 of between about 0.002 inches to 0.010 inches.

Alternately, for example, each receiver 56 could be a triangular tooth (not shown) which extends outwardly from the first edge 28 and the protruding lip 58 could be replaced with an indentation (not shown) into the second edge 30.

Referring to FIG. 4, each band 22 may also includes a retainer 66 for holding each band 22 in substantially the contracted configuration 48 until sufficient force is applied to the inner surface 32 of the band 22 to release the retainer 66 and allow expansion of the band 22. In the embodiments shown in the Figures, the retainer 66 is an adhesive which is disposed in an aperture 68 proximate the first end 36. The adhesive bonds the first end 36 to the outer surface 34 to hold the band 22 in the contracted configuration 48. An adhesive, such as NUVA-SIL 5088, which is sold by Loctite Corporation located in Newington, Conn., having a low shear strength and high tensile strength can be used so that the adhesive bond readily disengages upon inflation of a balloon 70. With this adhesive, a force of approximately 10 to 100 P.S.1. is required to disengage the adhesive.

Returning to FIG. 2, it may be seen that each band 22 is distributed along a substantially common central axis 62 to form the stent 10. The first end 36 of each band 22 is interconnected by the first elongated strip 24. The positioning of the first elongated strip 24 proximate the first end 36 of each band 22 allows the first elongated strip 24 to also function as a stop which prevents each band 22 from expanding farther than the fully expanded configuration 44. In the embodiment shown in FIG. 6, the first elongated strip 24 interconnects all of the bands 22 in the stent 10. In an alternate embodiment shown in FIG. 7, the first elongated strip 24 includes a first section 74 and a second section 76.

In this embodiment, the first section 74 interconnects a first set 78 of bands 22 while the second section 76 interconnects a second set 80 of bands 22. This allows for more conformability to the vessel post deployment, enables deployment with minimal twisting, and lowers deployment pressure. In this embodiment, the first set 78 and the second set 80 each includes five bands 22. However, for example, the first set 78 can include four bands 22 while the second set 80 includes six bands 22.

Similarly, each second end 38 of each band 22 is interconnected by the second elongated strip 26. As can best be seen in FIGS. 6 and 7, the second elongated strip 26 is actually positioned between the first end 36 and the second end 38. More specifically, the second elongated strip 26 is positioned between approximately two-thirds to three-quarters of the distance between the first end 36 and the second end 38.

Importantly, when the stent 10 is configured into the fully expanded configuration 44 shown in FIG. 2 or the contracted configuration 48 shown in FIG. 4, the first elongated strip 24 is positioned relatively close to second elongated strip 26. As a result, the stent 10 is free to flex along an axis defined by the first elongated strip 24 and the second elongated strip 26. This allows the stent 10 to be inserted through curved or winding vessels 12 and allows the stent 10 to be expanded to support curved or winding vessels 12.

Referring to FIG. 1, an outer surface 71 of one of the elongated strips 24, 26 and more preferably the first elongated strip 24 includes a marker 69 which is clearly and easily visible with an x-ray (not shown) to indicate the location of the stent 10 in the vessel. For example, the marker 69 can be a flat gold wire which is spot welded to the stent 10. The gold wire is clearly visible from an x-ray while the remaining portions of the stent 10 appear only faintly on the x-ray. Preferably, a marker 69 is located proximate the distal band 57 and a marker 69 is located proximate the proximal band 59 so that the location of the stent 10 can be precisely determined.

The stent 10 may be fabricated within a range of diameters and overall lengths. Specifically, stents 10 which range in diameter from about one millimeter to six millimeters (1.0 mm–6.0 mm) and range in length from about ten millimeters to forty millimeters (10.0 mm–40.0 mm) have been found to be preferable. The diameter of a given stent 10 is determined, by the length between the first end 36 and the second end 38 of each band 22. The overall length, however, depends on the number of bands 22, the width between the first edge 28 and the second edge 30 of each band 22, and the spacing between the bands 22. Specifically, stents 10 having a width between first edge 28 and the second edge 30 of each band 22 of between about 0.025 millimeters to 1.25 millimeters and spacing between bands 22 of between about 0.025 millimeters to 2.5 millimeters are acceptable.

The embodiment shown in the Figures includes a sequence of ten bands 22. Alternatively, for example, the stent 10 can include a sequence of twenty bands (not shown). It will be appreciated that longer or shorter embodiments with additional or less bands 22 are envisioned by the present invention. Structurally, longer sequences of bands 22 may require additional support. Therefore, in cases where longer sequences of bands 22 are needed, it may be desirable to increase the width between the first edge 30 and the second edge 32 of one or more bands 22 and/or provide additional interconnections between one or more of the bands 22.

Additionally, in the embodiment shown in FIG. 7, each band 22 includes a plurality of band apertures 82. This allows each band 22 to be widened and adjacent bands moved closer together. The resulting stent 10 has less coverage of the vessel 12, increased arterial support, increased blood access to the vessel 12, better angiographic appearance, smoother feel, and easier processing.

MANUFACTURING

One method for fabricating a stent 10 according to the present invention begins by photo-chemical milling of a flat sheet of full hard, implant grade, 316L stainless steel. The photo-chemical milling is used to produce the bands 22, the first elongated strip 24, the second elongated strip 26, the tabs 52, 54, the receivers 56 and the protruding section 58 in an unrolled configuration shown in FIGS. 6 and 7. Next, the tabs 52, 54 are annealed to provide flexibility to the tabs 52, 54. After annealing of the tabs 52, 54, the flat sheet is finished using electropolishing or some other surface treatment known by those skilled in the art and the markers 69 are manufactured into the first elongated strip 24.

Subsequently, the flat sheet can be rolled around a mandrel (not shown) to form the stent 10 having an equilibrium configuration 46 which is substantially equal to the diameter of the mandrel. Preferably, the flat sheet is rolled so that movement of each band 22 between the contracted configuration 48 and the fully expanded configuration 44 is substantially within the elastic limits of each band 22. Further, each band 22 is rolled so that the equilibrium configuration 46 is substantially between the contracted configuration 48 and the fully expanded configuration 44.

For example, the flat sheet could be rolled around a mandrel (not shown) having a diameter which is approximately equal to 1.45 millimeters. Thus, the stent 10 would have a diameter 42 at the equilibrium configuration 46 of approximately 1.45 millimeters. In this embodiment, each band 22 of the stent 10 is designed to have a diameter 42 at the contracted configuration 48 of approximately 1.25 millimeters, a diameter 42 at the intermediate expanded configurations 50 within the range of between about 1.8 millimeters to about 2.5 millimeters and a diameter 42 at the fully expanded configuration 44 of about 2.6 millimeters. Also, for this embodiment, each band 22 has a diameter 42 of approximately 1.25 millimeters at the compressed elastic limit and a diameter 42 of approximately 3.1 millimeters at the expanded elastic limit.

Depending upon the requirements of the operation, the diameter 42 of the equilibrium configuration 46 can be designed to be only slightly greater than the diameter 42 at the contracted configuration 48 or can be designed to be only slightly less than the diameter 42 at the intermediate expanded configurations 50.

Next, the first tab 52 and the second tab 54 are bent over the outer surface 34 to secure the tabs 52, 54 to their respective bands 22. The tabs 52, 54 were previously annealed so that they do not break from the band 22 during this procedure. Since the tabs 52, 54 are bent after the bands 22 are rolled, the stent 10 is relatively easy to manufacture.

Subsequently, after rolling the stent to the contracted configuration 48, the stent 10 can be passivated, i.e., applying an oxide surface coating which is corrosion resistant and is relatively inert. Additionally, other coatings may be applied to the stent 10, such as anti-coagulant coatings, neointimal proliferation inhibitors, or radioactive coatings.

Due to the differences in thermal expansion, coefficients of friction and dimensional creep of the stent 10 and the balloon catheter 70, many prior art stents (not shown) are covered with a sheath (not shown) to prevent the stent 10 from coming off of the balloon catheter 70 during shipping and during insertion into the vessel 12. However, the use of a sheath complicates the use and positioning of the stent 10 in the vessel 12. To solve this problem, as represented in FIG. 4, a coating 84 can be applied over the stent 10 to inhibit movement between the stent 10 and the balloon catheter 70 prior to placement of the stent 10 in the vessel 12.

The coating 84 can be made of a curable polymer material such as a hydrophilic coating. When dry, the hydrophilic coating acts as an adhesive that adheres to polymer substrates and produces a high friction surface. When the hydrophilic coating is exposed to an aqueous solution, it becomes very slick and loses its shear strength to metallic surfaces. Thus, while dry, i.e., while outside the body and during shipping, the stent 10 is retained in place by the coating 84. After insertion in the body, the hydrophilic coating becomes slippery and releases the stent 10 so it can be expanded by the balloon catheter 70. A suitable hydrophilic coating is sold by BSI Corporation, location in Eden Prairie, Minn. The hydrophilic coating can be applied directly to the intended bond area or can be dip coated over substantially the entire stent 10 and the balloon catheter 70. The coating 84 shown in FIG. 4 is merely exemplary.

Now the stent 10 in the contracted configuration 48 (shown in FIG. 4) is ready for placement into the vessel 12.

OPERATION

Insertion of the stent 10 into the vessel 12 (or other part of the body) begins by placement of the stent 10 in the contracted configuration 48 over a deflated, inflatable balloon catheter 70. Once the stent 10 in the contracted configuration 48 of FIG. 4, is mounted on the inflatable balloon 70, a guidewire 72 and a placement catheter (not shown) are inserted into the vessel 12 where the stent 10 is to be deployed. The stent 10 and balloon 70 are then advanced along the guidewire 72 through the placement catheter (not shown) and into the vessel 12 and toward a target site. The markers 69 on the stent 10 allows the doctor to precisely position the stent 10 at the target site.

Once the balloon 70 and the stent 10 are placed substantially adjacent the target site, the balloon 70 is partially inflated. The partial inflation of the balloon 70 expands the stent 10 from the contracted configuration 48 to the equilibrium configuration 46 and releases the bands 22 from the balloon.

Once the bands 22 are released, the resilient material of the bands 22 causes the bands 22 to move from the contracted configuration 48 of FIG. 4 towards equilibrium configuration 46 of FIG. 3. Since the contracted configuration 48 is within the elastic limits of the band 22, each band 22 will not plastically deform and will return proximate to the equilibrium configuration 46 absent any external force from the vessel 12.

Subsequently, the balloon 70 may then be more fully inflated to expand each of the bands 22 as required. As each band 22 expands, the first tab 52 sequentially engages the receivers 56. During this action, the second tab 54 interacts with the protruding section 58 to securely draw the first tab 52 into the receiver 56. Also, the relief 64 allows the first and second tabs 52, 54 to separate as the first tab 56 moves over the receivers 56 and pull together when the first tab 52 engages a specific receiver 56.

In particular, each band 22 may be expanded until the first tab 52 engages one of the receivers 56. Depending upon which receiver 56 is engaged by the first tab 52, each band 22 can be positioned in one of the intermediate expanded configurations 50 as shown in FIG. 1 or the fully expanded configuration 44 of FIG. 2. Importantly, each band 22 may be individually expanded to reach an individual degree of expansion to suit the specific need of the patient. In this fashion, the stent 10 may be adapted to support tapered or otherwise irregular vessels 12. Once the stent 10 has been properly expanded, the balloon 70 may be deflated and the balloon 70 and placement catheter 72 may be removed, completing the procedure.

Since each band 22 is expanded within its elastic limits, each band 22 wants to return its equilibrium configuration 46. This causes the first tab 52 to securely engage the specific receiver 56 and securely retain the stent 10 in position.

In some cases, internal pressure within a vessel 12 may exceed the strength of a particular vascular segment. In such cases, the present invention may be reconfigured to add a thin layer of substrate or material (not shown), such as Rayon, over the bands 22 to form a reinforcing stent (not shown). Insertion of the modified reinforcing stent generally follows the operational sequence outlined in the preceding paragraphs.

While the particular expandable stent 10 as herein shown and disclosed in detail is fully capable of obtaining the objects and providing the advantages herein before stated, it is to be understood that this is merely illustrative of the presently preferred embodiments of the invention. For example, in some embodiments, the balloon 70 may be replaced with some other device (not shown), such as a small actuator, which can move the stent 10 from the contracted configuration 48 to one of the intermediate expanded configurations 50 or the fully expanded configuration 44 in the vessel 12. Therefore, no limitations are intended to the details of construction or design herein shown other than as described in the appended claims.

What is claimed is:

1. A stent for placement in a vessel, the stent comprising at least one tubular shaped band, the band comprising:

a first end overlapping a portion of a second end and being moveable relative to the second end to reconfigure the band between at least a contracted configuration and a fully expanded configuration;

at least one notch positioned proximate a first edge of the band; and a first tab projecting from proximate the first edge, the first tab including an engagement section that extends substantially radially from proximate the first edge, the engagement section being adapted for engaging the notch.

2. The stent of claim 1 including a plurality of interconnected bands.

3. The stent of claim 2 including a first elongated strip interconnecting at least some of the bands proximate the first end of the bands and a second elongated strip interconnecting at least some of the bands intermediate the first end and the second end of the bands.

4. The stent of claim 3 wherein the first elongated strip comprises a first section interconnecting a first set of bands and a second section interconnecting a second set of bands.

5. A stent for placement in a vessel, the stent comprising at least one tubular shaped band, the band comprising:

a first end overlapping a portion of a second end and being moveable relative to the second end to reconfigure the band;

at least one notch positioned proximate a first edge of the band, each notch having a notch depth;

a first tab positioned proximate the first edge, the first tab being adapted for engaging the notch; an outwardly protruding section extending from proximate a second edge of the band, opposite the notch; and a second tab extending from proximate the second edge, the second tab being adapted for interacting with the protruding section to draw the first tab into engagement with the notch.

6. The stent of claim 5 wherein the outwardly protruding section extends a section distance which is substantially equal to the notch depth from the second edge of the band.

7. The stent of claim 5 including a plurality of interconnected bands.

8. The stent of claim 5 wherein the first tab cantilevers from the first edge and the first tab includes an engagement section that extends substantially radially from proximate the first edge for engaging the notch.

9. A stent for placement in a vessel, the stent comprising at least one band, the band comprising:

a first end overlapping a portion of a second end and being moveable relative to the second end to reconfigure the band between at least a contracted configuration and a fully expanded configuration;

at least one receiver positioned proximate a first edge of the band;

a first tab positioned proximate the first edge, the first tab including an engagement section which is adapted for engaging the receiver to inhibit the band from retracting towards the contracted configuration; and a relief positioned proximate the first tab, the relief facilitating movement of the engagement section relative to the first edge of the band so that the first tab moves past the receiver during movement of the band towards the fully expanded configuration.

10. The stent of claim 9 wherein at least a portion of the first tab is annealed to facilitate movement of the first tab past the receiver.

11. The stent of claim 9 including a plurality of interconnected bands.

12. The stent of claim 9 further comprising a second tab which cantilevers from the second edge; wherein the relief facilitates movement of the first tab relative to the second tab; wherein the first tab cantilevers from the first edge and the engagement section extends substantially radially from proximate the first edge.

13. A stent for placement in a vessel, the stent comprising:

a plurality of bands, each band having a first end overlapping a portion of a second end and being moveable relative to the second end to reconfigure the band;

a first elongated strip interconnecting at least some of the bands proximate the first end of these bands; and a second elongated strip interconnecting at least some of the bands intermediate the first end and the second end of these bands.

14. The stent of claim 13 wherein the first elongated strip comprises a first section interconnecting a first set of bands and a second section interconnecting a second set of bands.

15. The stent of claim 13 wherein at least one of the bands includes a plurality of notches positioned proximate a first edge of the band and a first tab cantilevering from proximate the first edge, the first tab including an engagement section that extends substantially radially from proximate the first edge, the engagement section being adapted for engaging the at lease one of the notches.

16. The stent of claim 13 wherein the band includes a plurality of notches positioned proximate a first edge of the band, a first tab cantilevering from proximate a first edge of the band, and a second tab cantilevering from proximate a second edge of the band; wherein the first tab includes an engagement section which is movable relative to the second tab and is adapted to engage at least one of the notches.

17. A stent for placement in a vessel, the stent comprising a plurality of interconnected, tubular shaped bands, at least one of the bands comprising:

a first end overlapping a portion of a second end and being moveable relative to the second end to reconfigure the band;

a plurality of spaced apart notches formed proximate a first edge of the band, proximate the first end, each notch having a notch depth;

an outwardly protruding section extending a section distance which is substantially equal to the notch depth from proximate a second edge of the band opposite at lease one of the notches;

a first tab extending from proximate the first edge, proximate the second end, the first tab extending upwardly and around at least a portion of an outer surface of the band; and a second tab extending from proximate the second edge, proximate the second end, the second tab extending upwardly and around at least a portion of the outer surface of the band for interacting with the protruding section to draw the first tab into engagement with at least one of the notches.

18. A stent for placement in a vessel, the stent comprising at least one tubular shaped band comprising a first end overlapping a portion of a second end and being moveable relative to the second end to reconfigure the band between a contracted configuration and an expanded configuration, the band being made from a resilient material that is formed so that movement between the contracted configuration and the expanded configuration is substantially within the elastic limits of the band and is formed so that an equilibrium configuration of the band is substantially between the contracted configuration and the expanded configuration.

19. The stent of claim 18 wherein the band includes at least one notch disposed proximate a first edge, and a first tab cantilevering from proximate the first edge, the first tab including an engagement section that extends substantially radially from the first edge, the engagement section being adapted to engage the notch and inhibit the band from retracting towards the contracted configuration.

20. The stent of claim 18 wherein the band includes at least one notch disposed proximate a first edge and a first tab cantilevering from proximate the first edge, the first tab including an engagement section which is adapted to engage the notch and inhibit the band from retracting towards the contracted configuration, the engagement section being movable relative to the first edge of the band to facilitate movement of the first tab past the notch.

21. A stent prepared by a process comprising the steps of:
providing a band in a substantially flat sheet of resilient material, the band having a first end and a substantially opposed second end, the band including a first tab cantilevering from the band and a notch;

rolling the sheet so that the first end of the band overlaps at least partly the second end; and bending the first tab relative the first edge of the band so that an engagement section of the first tab engages the notch.

22. The stent of claim 21 wherein the step of providing a band includes the band having (i) a second tab which cantilevers from the band and (ii) an outwardly protruding section extending a section distance which is substantially equal to a notch depth of the notch, opposite the notch; wherein the process includes the step of bending the second tab relative to the first tab.

23. A stent for placement in a vessel, the stent comprising at least one tubular shaped band, the band comprising:

a first end overlapping a portion of a second end and being moveable relative to the second end to reconfigure the band between at least a contracted configuration and a fully expanded configuration;

a notch positioned proximate a first edge of the band; and a first tab cantilevering from proximate the first edge, the first tab including an engagement section which is adapted to move relative to the first edge of the band, the engagement section being adapted to engage the notch.

24. The stent of claim 23 wherein the engagement section extends substantially radially from proximate the first edge.

25. The stent of claim 23 including a plurality of interconnected bands.

26. The stent of claim 23 further comprising a second tab cantilevering from proximate a second edge of the band, the second tab engaging the second edge of the band and pulling the engagement section into the notch.

27. A stent for placement in a vessel, the stent comprising a plurality of interconnected, tubular shaped bands, at least one of the bands comprising:

a first end overlapping a portion of a second end and being moveable relative to the second end to reconfigure the band;

a plurality of spaced apart notches formed proximate a first edge of the band; and a first tab and a second tab secured to the band, the first tab cantilevering away from the band so that an engagement section of the first tab is adapted to move relative to the second tab, the engagement section being adapted to engage at least one of the notches.

28. The stent of claim 27 wherein the engagement section extends substantially radially from proximate the first edge of the band and the second tab engages a second edge of the band.

\* \* \* \* \*

UNITED STATES PATENT AND TRADEMARK OFFICE
CERTIFICATE OF CORRECTION

PATENT NO.   : 5,876,419
DATED        : March 2, 1999
INVENTOR(S)  : Kenneth W. Carpenter et al.

It is certified that error appears in the above-identified patent and that said Letters Patent is hereby corrected as shown below:

```
Column 12, Line 65
DELETE
[the at lease]
INSERT
--at least--

Column 13, Line 20
DELETE
[lease]
INSERT
--least--
```

Signed and Sealed this

Seventeenth Day of August, 1999

Attest:

Attesting Officer

Q. TODD DICKINSON

Acting Commissioner of Patents and Trademarks